(12) United States Patent
Maekawa et al.

(10) Patent No.: US 6,290,851 B1
(45) Date of Patent: Sep. 18, 2001

(54) MICROORGANISMS-IMMOBILIZED MAGNETIC CARRIERS, A PROCESS FOR PRODUCING THE CARRIERS AND A METHOD OF TREATING WASTEWATER

(75) Inventors: Takaaki Maekawa; Mitsuaki Kuroshima, both of Ibaraki (JP)

(73) Assignee: Japan Science and Technology Corporation (JP)

( * ) Notice: Subject to any disclaimer, the term of this patent is extended or adjusted under 35 U.S.C. 154(b) by 0 days.

(21) Appl. No.: 09/491,335

(22) Filed: Jan. 25, 2000

Related U.S. Application Data (62) Division of application No. 09/107,380, filed on Jun. 30, 1998, now Pat. No. 6,043,068.

(30) Foreign Application Priority Data

Jul. 2, 1997 (JP) .................................................... 9-177269

(51) Int. Cl.⁷ .............................. C02F 1/48; C12N 11/04; H01F 1/26
(52) U.S. Cl. .......................... 210/616; 210/695; 210/767; 435/182; 252/62.54
(58) Field of Search .................................... 210/616, 615, 210/617, 695, 767; 435/180, 181, 182; 252/62.54

(56) References Cited

U.S. PATENT DOCUMENTS 5,000,853 * 3/1991 Reischl et al. .

FOREIGN PATENT DOCUMENTS

| 3228477 | 2/1984 | (DE) . |
| 0522322 | 1/1993 | (EP) . |
| 0881287 | 12/1998 | (EP) . |
| 11-18765-A1 * | 1/1999 | (JP) . |

* cited by examiner

Primary Examiner—Chester T. Barry
(74) Attorney, Agent, or Firm—Fish & Richardson P.C.

(57) ABSTRACT

The present invention relates to magnetic carriers in which microorganisms requiring carriers for their growth in the step of treating wastewater have been immmobilized, a process for producing the carriers and a method of treating wastewater. The present invention provides microorganisms-immobilized carriers with a high amount of microorganisms immobilized for use in wastewater treatment, the movement of which is controllable in a treatment chamber by magnetic force. Further the present invention provides a process for producing said carriers easily and a method for treating wastewater efficiently.

7 Claims, 7 Drawing Sheets

MICROORGANISMS-IMMOBILIZED MAGNETIC CARRIERS, A PROCESS FOR PRODUCING THE CARRIERS AND A METHOD OF TREATING WASTEWATER

The present application is a divisional (and claims the benefit of priority under 35 USC 121) of U.S. patent application Ser. No. ("USSN") 09/107,380, filed on filed Jun. 30, 1998 now 6,043,068, which claims the benefit of priority under 35 U.S.C. § 119 of Japanese patent application number 17762/1997, filed Jul. 2, 1997. These applications are explicitly incorporated herein by reference in their entirety and for all purposes.

FIELD OF THE INVENTION

The present invention relates to magnetic carriers in which microorganisms requiring carriers for their growth in the step of treating wastewater have been immobilized, a process for producing the carriers and a method of treating wastewater.

BACKGROUND OF THE INVENTION

For wastewater treatment, methods using microorganisms-immobilized carriers have been put to practical use widely. However, it is revealed that there are drawbacks such as damages of carriers and microorganisms caused by stirring in a carrier-suspending chamber, pressure loss in a fixed-bed biomembrane chamber, outflow of carriers in a fluidized-bed biomembrane chamber, and carrier floating caused by gases generated in the carriers. To overcome these drawbacks, it is effective to control the movement of carriers by utilizing magnetic force to stably retain a predetermined amount of carriers in a treatment chamber.

The magnetic carriers have been developed for the purpose of rapid separation and recovery of immobilized materials, e.g. biologically active substances such as enzymes etc. and animal cells etc., by magnetism from the outside. For example, JP-A No. 1102/1990 and JP-B No. 16164/1993 disclose immobilized magnetic carriers in which biologically active substances etc. are immobilized by first forming a magnetic body-containing nucleus, then laminating a polymer layer on the outside thereof, and immobilizing biologically active substances etc. onto the polymer layer of the magnetic carriers by an adsorption method, covalent bonding method, ionic bonding method, entrapment method, cross-linking method etc. For such magnetic carriers, it is reported that the thickness of the polymer layer should be reduced to 30% or less of the diameter of carriers as a whole to permit the ultra-paramagnetic body inside the carriers to work sufficiently (JP-B No. 16164/1993). However, in the case of microorganisms-immobilized magnetic carriers for wastewater treatment, if the thickness of the polymer is limited to 30% or less, the amount of microorganisms to be immobilized thereon is limited, and thus the polymer layer with such thickness does not appear to be effective.

Further, these conventional magnetic carriers are mainly directed to separation and recovery, so a process for their production includes adjustment of the content of the ultra-paramagnetic body, adjustment of specific gravity, formation of the polymer layer etc. and is thus complicated. On the other hand, the separation and recovery of the microorganisms-immobilized carriers is a secondary object in wastewater treatment, so there is demand for a simple and economically advantageous production process in order to eliminate these complicated steps.

SUMMARY OF THE INVENTION

An object of the present invention is to provide microorganisms-immobilized carriers with a high amount of microorganisms immobilized for use in wastewater treatment, the movement of which is controllable in a treatment chamber by magnetic force.

Another object of the present invention is to provide a process for efficiently producing said carriers.

A further object of the present invention is to provide a method for efficiently treating wastewater.

The present invention relates to microorganism-immobilized magnetic carrier comprising an ultra-paramagnetic body and microorganism entrapped in a polyacrylamide gel. In place of said polyacrylamide gel, other polymer gels such as polyvinylalcohol (PVA) gel can be used.

Further, the present invention relates to a process for producing the microorganism-immobilized magnetic carriers as, which comprises passing an aqueous solution (A) containing acrylamide, a gelation promoter, sodium alginate and an ultra-paramagnetic body between an outer and an inner tubes in a double-tubular nozzle consisting of an outer tube and an inner tube while passing a microbial suspension (B) through said inner tube to mix said aqueous solution (A) with said suspension (B) at the top of said double-tubular nozzle to form droplets, and dropping said droplets into an aqueous solution (C) containing calcium formate.

Furthermore, the present invention relates to a method for treating wastewater, in which said microorganisms-immobilized magnetic carriers are used.

BRIEF DESCRIPTION OF THE DRAWINGS

The meanings of symbols are as follows: 1, magnetic carriers; 2, treatment chamber; 3, magnet; 4, magnetic coil; 5, metal core; 6, culture chamber; 7, electromagnet; 8, partition plate; and 9, permanent magnet.

DETAILED DESCRIPTION OF THE INVENTION

The present invention is described in detail below.

The microorganisms-immobilized magnetic carriers of the present invention comprise an ultra-magnetic body and microorganisms entrapped in polyacrylamide gel. When acrylamide monomers are polymerized in an aqueous solution in the presence of a gelation promoter, they form porous polyacrylamide gel. The resulting gel serves as carriers which can immobilize a large amount of microorganisms and have a shape suitable for growth of microorganisms as well as for release of generated gases, thus being advantageous for wastewater treatment etc.

The microorganism-immobilized magnetic carriers containing PVA gel in place of said polyacrylamide gel can also be used for the same purpose. Such magnetic carriers can be produced using PVA in place of said acrylamide monomer. In this case, if beads are formed by the freezing method described below, the gelation promoter is not necessary.

The ultra-paramagnetic body is a magnetic body which, like fine particles of a ferromagnetic body and ferrimagnetic body, is free of residual magnetization even if once placed in a magnetic field. Thus, unlike a usual magnetic body, they do not attach to each other after taken from a magnetic field. This property is preferable for wastewater treatment, and such an ultra-magnetic body includes fine powder of iron oxide such as magnetite, ferrite etc. Their preferable particle diameters are usually in the range of about 100 Å to 1 μm.

The microorganism is not particularly limited, so long as it can be used in wastewater treatment. For example, activated sludge or anaerobically digestible sludge can be used. Such sludge can be collected from, for example, a sewage disposal plant.

When the microorganism-immobilized magnetic carriers of the present invention are used in fixed-bed treatment or fluidized-bed treatment, they are preferably in the form of spherical beads. In this case, the diameters of beads are preferably 2.0 to 5.0 mm.

The microorganism-immobilized magnetic carriers in the form of spherical beads of uniform size can be produced in, for example, the following manner using a double-tubular nozzle consisting of an outer tube and an inner tube inserted into said outer tube.

An aqueous solution (A) containing acrylamide, a gelation promoter, sodium alginate and an ultra-paramagnetic body is passed between the outer and inner tubes in the double-tubular nozzle. At the same time, a microbial suspension (B) is passed through the inner tube of the double-tubular nozzle. They are mixed instantaneously at the outlet of the nozzle to form droplets. The inner diameter of the outlet of the outer tube is preferably 2.0 to 3.0 mm. The inner diameter of the outlet of the inner tube is preferably 1.0 to 1.5 mm. The difference between the inner diameter of the outer tube and the outer diameter of the inner tube is preferably at least 0.3 mm. The flow rate of the aqueous solution (A) and the suspension (B) is controlled so that they form droplets in the outlet of the nozzle. The supplied suspension (B): aqueous solution (A) ratio in volume is controlled preferably at a ratio of about 3:1 to 5:4, more preferably about 5:2.5 to 5:3, using, for example, a roller pump.

The gelation promoter to be added to the aqueous solution (A) includes cross-linking agents such as N,N'-ethylene-bis-acrylamide etc. and polymerization initiators such as N,N,N',N'-tetraethylethylenediamine etc. These can be used singly or in combination thereof. In particular, a combination of N,N'-ethylene-bis-acrylamide and N,N,N',N'-tetraethylethylenediamine is preferably used. The concentration of acrylamide monomers in the aqueous solution (A) is preferably 15 to 17% (w/v). The amount of N,N'-ethylene-bis-acrylamide employed is preferably 4.0 to 5.5 parts by weight for 100 parts of acrylamide. The amount of N,N,N',N'-tetraethylethylenediamine employed is preferably 6.0 to 7.0 parts by weight for 100 parts of acrylamide.

Sodium alginate is added to the aqueous solution (A) so that when the above-mentioned droplets are dropped into the aqueous solution (C) containing calcium formate, a film of sodium alginate is instantaneously formed to give beads. The concentration of sodium alginate in the aqueous solution (A) is preferably 0.5 to 0.9% (w/v).

The amount of the ultra-paramagnetic body added to the aqueous solution (A) varies depending on the type of polymer employed and the forming method. When polyacrylamide gel is used as the polymer, the concentration of the ultra-paramagnetic body in the aqueous solution (A) is preferably 1 to 3% (w/v). When PVA gel is used as the polymer, the final concentration of the ultra-paramagnetic body in beads is preferably 10 to 50 g/L.

The suspension (B) includes, for example, concentrated sludge with volatile floating materials at a content of about 0.5 to 4.0%, preferably about 1 to 3%, obtained by centrifugation-sedimenting activated sludge collected from a sewage disposal plant.

Droplets formed at the outlet of the nozzle are dropped into the aqueous solution (C) containing calcium formate. The concentration of calcium formate in the aqueous solution (C) is preferably 2.0 to 4.0% (w/v). For the purpose of strengthening a film on beads, ammonium persulfate etc. are preferably added to the aqueous solution (C). In this case using ammonium persulfate, the concentration of ammonium persulfate in the aqueous solution (C) is preferably 0.3 to 0.6% (w/v). When the droplets are dropped, a film of calcium alginate is formed instantaneously to give granular beads. In a mixture of the aqueous solution (A) and the suspension (B) entrapped in said film of calcium alginate, acrylamide monomers are cross-linked with cross-linking agents such as N,N'-ethylene-bis-acrylamide etc. to be polymerized to form a gel, while the ultra-paramagnetic body and the microorganisms are entrapped in the gel. This reaction is usually completed in about 30 minutes to 1 hour. In this manner, the microorganism-immobilized magnetic carriers of the present invention entrapped in a film of calcium alginate is obtained.

If PVA gel is used in place of polyacrylamide gel as the polymer, the droplets are dropped into the aqueous solution (C) to form spherical beads which are immediately frozen and left as such, whereby cross-linking of the polymer and entrapped immobilization of microorganisms can be effected. This method is called the freezing method, which is known to those skilled in the art. If this freezing method is used, the gelation promoter is not needed.

The film of calcium alginate formed outside the carriers can be removed by dissolving it in phosphate buffer etc., whereby porosity of the carriers can be improved.

In producing the microorganism-immobilized magnetic carriers, it is preferable for the aqueous solution (A) and the aqueous solution (C) to be previously cooled at about 3 to 5° C. in order to prevent damage to the microorganism caused by chemical reaction heat.

After the microorganism-immobilized magnetic carriers of the present invention are produced, the microorganism is initially retained in the inside of the carriers. However, as waste-treatment etc. proceeds, the microorganism is attached and grows on the porous surface of the carriers. When treatment efficiency has reached a steady state, a film of microorganisms has been formed even on the surface of the carriers.

Wastewater can be treated efficiently by using the microorganism-immobilized magnetic carriers of the present invention. The method of treating wastewater is not particularly limited, which includes the conventional methods such as the batch treatment method, the fixed-bed treatment method and the fluidized-bed treatment method. The microorganism-immobilized magnetic carriers of the present invention can be used effectively in any of the conventional methods.

For example, if the microorganism-immobilized magnetic carriers of the present invention are used in batch treatment, the magnetic carriers suspended in a batch treatment chamber can be aggregated in a short time by applying a magnetic field from the bottom of the treatment chamber, as shown in Example 3 below. Thereby, the time for the aggregation/precipitation step can be reduced significantly. In addition, the amount of treated water or sludge to be drawn can also be set at a predetermined amount. In this manner, complicated steps such as the management of treated water and sludge and the operation of solid-liquid separation, which conventionally rely on the experience of the manager, can be omitted.

Further, for example, as shown in Examples 4 and 5 below, the microorganism-immobilized magnetic carriers of the present invention can be moved without stirring said magnetic carriers in a treatment chamber by applying a magnetic field from the outside of the treatment chamber. Thereby, the carriers and microorganisms can be prevented from damage caused by a stirring blade or the shear strength of a water stream etc. Therefore, although a considerable level of physical strength is conventionally required for such carriers so as to be resistant to stirring in suspending carriers, such high level of strength is not required for the carriers of the present invention. Further, a fluidized-bed biomembrane can be formed by moving the carriers constantly or at short intervals. The magnetic carriers can also be retained in a treatment apparatus by generating downward magnetic force by means of a magnetic coil. Thereby, pipe clogging, pump trouble etc. caused by an outflow of the carriers can be prevented.

In addition, for example, as shown in Example 6 below, formation of a short cut pathway for wastewater can be prevented and treatment efficiency is improved by giving vibration to a fixed bed of the microorganism-immobilized magnetic carriers of the present invention at predetermined intervals. By this vibration, sludge residue is also shaken off, thus clogging of the fixed bed as well as pressure loss can be prevented.

Further, for example, as shown in Examples 3 and 4 below, separation of air bubbles generated from the carriers can be promoted by forcibly immersing the magnetic carriers in treatment water by applying a magnetic field from the outside of the treatment chamber. Thereby, the individual carriers or the whole of the biomembrane can be prevented from floating.

Further, for example, as shown in Example 7 below, if the microorganism-immobilized magnetic carriers for wastewater treatment, while being cultured, is stocked in an arbitrary culture chamber, the magnetic carriers can be easily recovered as necessary by a strong electromagnet etc. Treatment efficiency can be improved by transferring the recovered magnetic carriers to another existing treatment chamber, and further, the carriers can also be used as seeding materials for another treatment.

Further, for example, as shown in Example 8 below, the carriers of the present invention can also be applied to treatment in a mixed culture system. The step of treating wastewater sometimes uses a microorganism-mixed culture system. In some cases, it is advantageous to adjust the proportion of the microbial mixture to a suitable ratio. Treatment efficiency can be improved as compared with treatment in the conventional mixed culture system, by culturing the magnetic carriers with different kinds of microorganisms immobilized thereon at a suitable ratio in chambers 1 and 2 respectively, and by intentionally controlling the particularly rate-determining treatment of microorganisms.

Further, for example, as shown in Example 9 below, a large amount of the magnetic carriers of the present invention can be adhered firmly to a permanent magnetic plate provided in an extrusion-type treatment chamber, thus permitting the microorganisms to be maintained at high density even if treated water is passed at considerably high rate, and thus treatment efficiency is improved.

The microorganisms-immobilized magnetic carriers of the present invention have a larger amount of microorganisms immobilized thereon. Further, movement of the carriers can be easily controlled by application of a magnetic field. Therefore, wastewater treatment can be conducted efficiently. In addition, according to the present invention, such microorganism-immobilized magnetic carriers can be easily produced.

EXAMPLES

The present invention is described below in more detail by the Examples, which however are not intended to limit the scope of the present invention.

Example 1

Production of Microorganisms-Immobilized Magnetic Carriers 12.5 g of acrylamide monomer, 0.6 g of N',N"-ethylene-bis-acrylamide, 1 ml of N,N,N',N'-tetraethylethylenediamine and 0.5 g of sodium alginate were dissolved in distilled water (final volume: 75 ml), and 1 to 3% (w/v) magnetite powder was suspended in the resulting solution, to prepare an aqueous solution (A).

On the other hand, sludge collected from a sewage disposal plant was sedimented by centrifugation such that it was concentrated to a volatile floating material content of about 1 to 3%, to give a microbial suspension (B).

The aqueous solution (A) was passed through the outer tube of a double-tubular nozzle (inner diameter of the outlet of the outer tube: 2.0 mm, the inner diameter of the outlet of the inner tube: 1.5 mm, the outer diameter of the outlet of the inner tube: 1.7 mm), while the suspension (B) was passed through the inner tube, so that the aqueous solution (A) and suspension (B) were instantaneously mixed at the top of the nozzle to form droplets. The aqueous solution (A) had previously been cooled to 4° C. The supplied suspension (B): aqueous solution (A) ratio in volume was controlled at a ratio of about 5:2.5 to 5:3 by using a roller pump. Droplets formed at the top of the double-tubular nozzle were then dropped into the aqueous solution (C) containing 3% calcium formate and 0.5% ammonium persulfate. The aqueous solution (C) had previously been cooled to 4° C. When the droplets were dropped into the aqueous solution (C), a film of calcium alginate was instantaneously formed to give granular beads. The beads were left in the aqueous solution (C) for 30 minutes to complete gelation by cross-linking reaction between the acrylamide monomer and the cross-linking agent such as N,N'-ethylene-bis-acrylamide etc., as well as entrapped immobilization of the ultra-paramagnetic body and microorganisms in the gel, in a mixture of the aqueous solution (A) and suspension (B) entrapped with a film of calcium alginate. The spherical bead-shaped microorganism-immobilized magnetic carriers with suitable strength, entrapped with a film of calcium alginate, were obtained in this manner.

The resulting magnetic carriers were washed with water and then immersed in 0.05 M potassium phosphate to elute calcium alginate from the surface layer in order to form more porous magnetic carriers. The spherical bead-shaped porous microorganism-immobilized magnetic carriers with an average particle diameter of about 3 mm were obtained in this manner.

Example 2
Production of Denitrificater-Immobilized PVA Magnetic Carriers for Elimination of N (Nitrate Nitrogen) from $NO_3^-$ Microorganism-immobilized magnetic carriers containing PVA gel in place of polyacrylamide gel and denitrificater as the microorganisms (referred to hereinafter as "denitrificater-immobilized PVA magnetic carriers") were prepared in the following manner.

Magnetite powder was suspended in 12% PVA aqueous solution containing 0.8% sodium alginate so as to give a final concentration of 15 g/L magnetite powder in beads, whereby an aqueous solution (A) was prepared.

On the other hand, a denitrificater culture was concentrated by centrifugation to about 50 g/L (in dry base) to give a microbial suspension (B).

Formation of spherical beads using the double-tubular nozzle was conducted in the same manner as in Example 1. In this case, the supplied suspension (B): aqueous solution (A) ratio in volume was controlled by a roller pump, so that 15 g/L magnetite and 10 g/L (in dry base) denitrificater were contained in the beads. The spherical beads obtained by dropping droplets into the aqueous solution (C) were frozen at −20° C. and left as such for 24 hours. By this treatment, gelation by cross-linking reaction as well as entrapped immobilization of the ultra-paramagnetic body and denitrificater into the resulting gel were completed. The spherical bead-shaped denitrificater-immobilized PVA magnetic carriers with suitable strength, entrapped with a film of calcium alginate, were obtained in this manner.

The resulting magnetic carriers were washed with water and then immersed in 0.05 M potassium phosphate to elute calcium alginate from the surface layer in order to form more porous magnetic carriers. The spherical bead-shaped porous denitrificater-immobilized PVA magnetic carriers with an average particle diameter of about 3 mm were obtained in this manner.

Figure 1A:
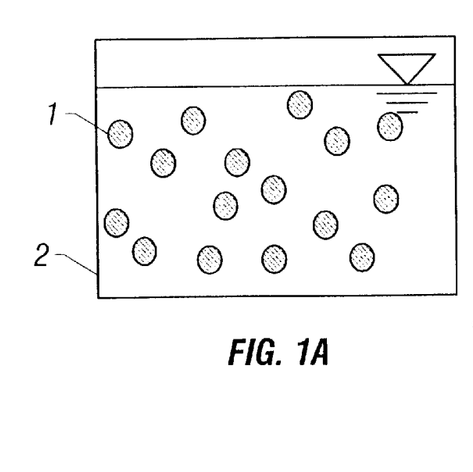
FIG. 1A to FIG. 1C are drawings illustrating the outline of a method of utilizing the microorganisms-immobilized magnetic carriers of the present invention in batch treatment of wastewater.
Figure 1B:
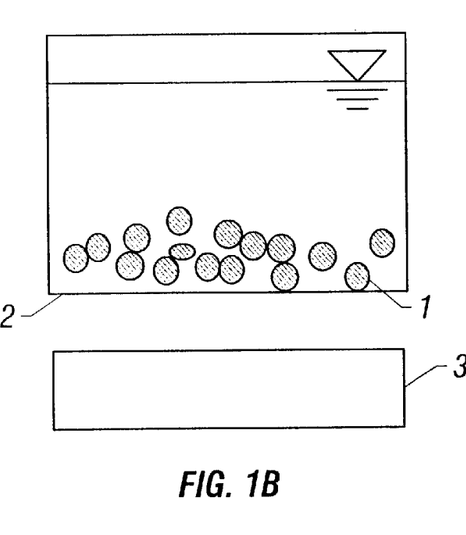
Figure 1C:
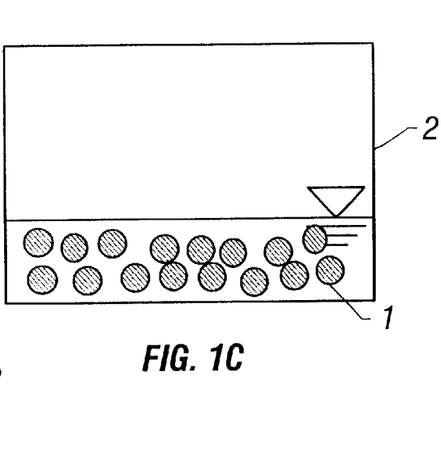

Example 3
Utilization of Microorganism-Immobilized Magnetic Carriers in Batch Treatment A wastewater suspension of the porous microorganisms-immobilized magnetic carriers 1 obtained in Example 1 was introduced into treatment chamber 2 (FIG. 1A). Then, the magnetic carriers 1 were forcibly aggregated and sedimented by applying a magnetic field upward from magnet 3 placed below the treatment chamber 2 (FIG. 1B). Then, the supernatant was drawn as treated water (FIG. 1C).

The magnetic carriers 1 remaining in the treatment chamber 2 can be used in seeding for subsequent batch culture. Further, the amount of microorganisms retained in the magnetic carriers 1 is almost constant, thus, the inflow of wastewater and the amount of treated water drawn corresponding thereto can be set at a constant value.

Example 4
Utilization of Microorganism-Immobilized Magnetic Carriers in Fluidized Bed Treatment (1)

Figure 2A:
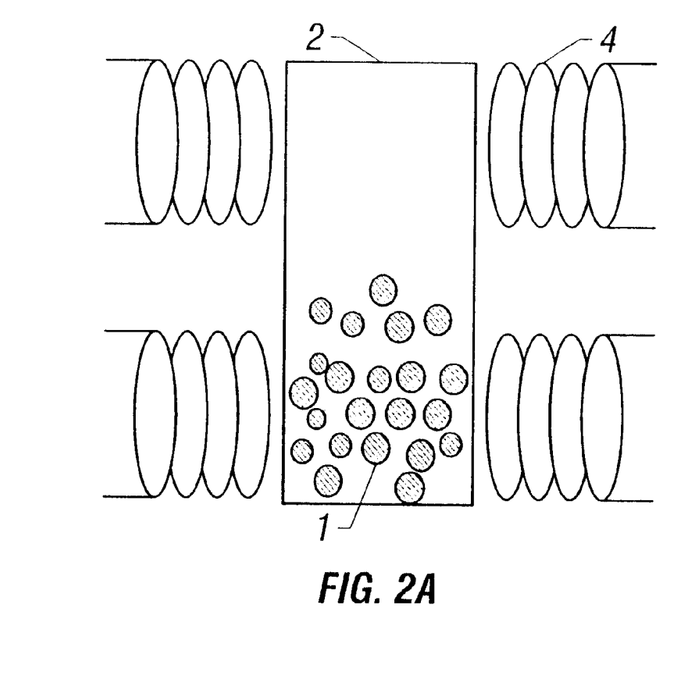
FIG. 2A and FIG. 2B are drawings illustrating the outline of a method of utilizing the microorganisms-immobilized magnetic carriers of the present invention in fluidized-bed treatment of wastewater.
Figure 2B:
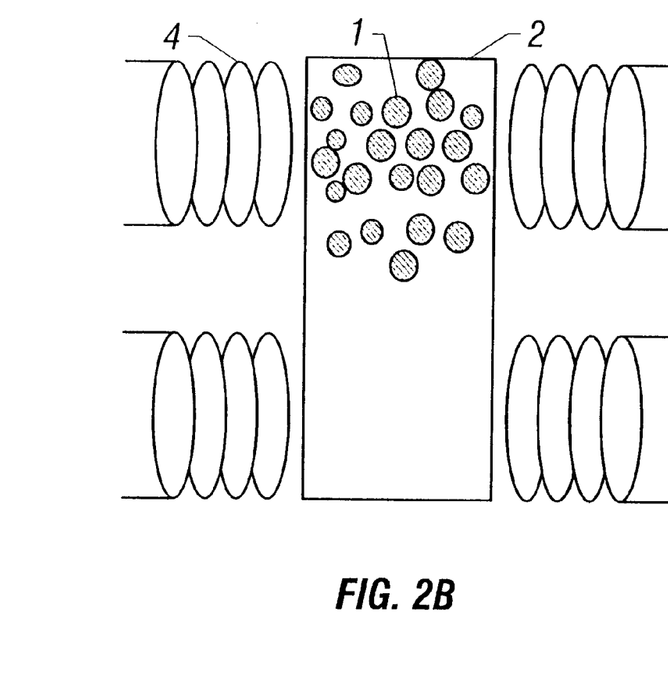

As shown in FIG. 2A, a wastewater suspension of the porous microorganisms-immobilized magnetic carriers 1 obtained in Example 1 was introduced into treatment chamber 2 provided therearound with four magnetic coils 4. Subsequently, and a magnetic field was generated by sending electric current into two magnetic coils 4 in a lower part of the treatment chamber, whereby the magnetic carriers 1 were moved downward (FIG. 2A). Then, a magnetic field was generated by sending electric current into two magnetic coils 4 in an upper part of the treatment chamber, whereby the magnetic carriers 1 were moved upward (FIG. 2B). By repeating this operation intermittently, the magnetic carriers 1 were moved to form a fluidized bed.

Example 5
Utilization of Microorganism-Immobilized Magnetic Carriers in Fluidized Bed Treatment (2)

Figure 3A:
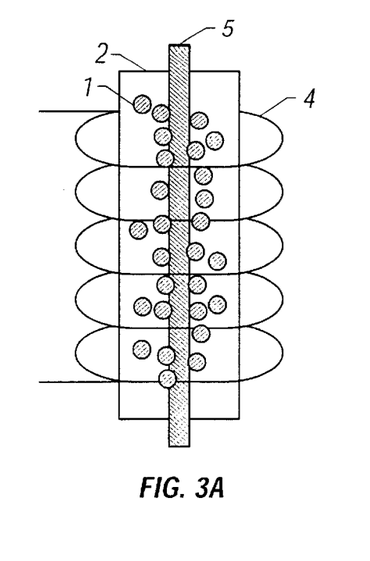
FIG. 3A and FIG. 3B are drawings illustrating the outline of a method of utilizing the microorganisms-immobilized magnetic carriers of the present invention in fluidized-bed treatment of wastewater.
Figure 3B:
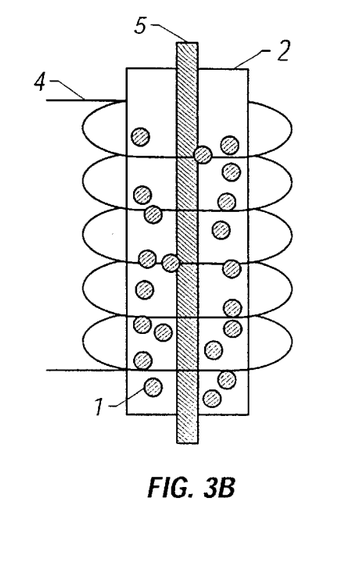

A wastewater suspension of the porous microorganisms-immobilized magnetic carriers 1 obtained in Example 1 was introduced into the treatment chamber 2 provided in the center with a metal core 5 and wound by magnetic coil 4. Subsequently, a magnetic field was generated by sending electric current into magnetic coil 4, whereby the magnetic carriers 1 were aggregated around the metal core 5 (FIG. 3A). When the electric current was stopped, the magnetic carriers 1 were dispersed (FIG. 3B). By repeating this operation intermittently, the magnetic carriers 1 were moved to form a fluidized bed.

Figure 4A:
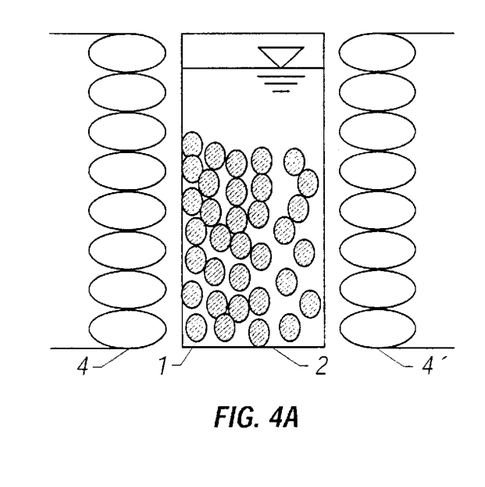
FIG. 4A and FIG. 4B are drawings illustrating the outline of a method of utilizing the microorganisms-immobilized magnetic carriers of the present invention in fixed-bed treatment of wastewater.
Figure 4B:
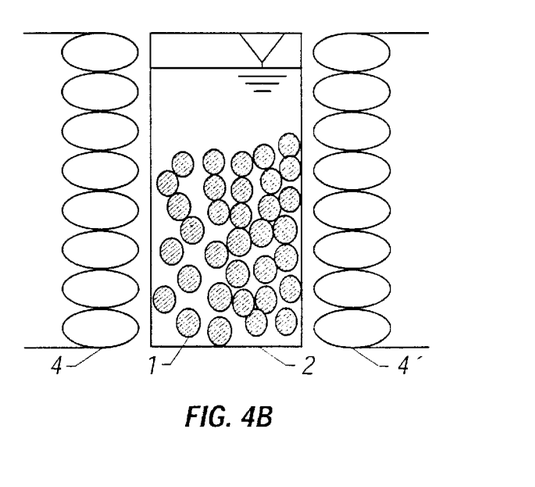

Example 6
Utilization of Microorganism-Immobilized Magnetic Carriers in Fixed Bed Treatment A wastewater suspension of the porous microorganisms-immobilized magnetic carriers 1 obtained in Example 1 was introduced to the treatment chamber 2 provided with magnetic coils 4 and 4' on both sides. Subsequently, a magnetic field was generated by sending electric current into only the left magnetic coil 4 outside the treatment chamber 2, whereby the magnetic carriers 1 became denser in the left in the treatment chamber 2 (FIG. 4A). Then, the electric current into the left magnetic coil 4 was stopped, and a magnetic field was generated by sending electric current into the right magnetic coil 4', whereby the magnetic carriers 1 became denser in the right in the treatment chamber 2 (FIG. 4B). By switching the state from A to B and then B to A intermittently at few-second intervals, formation of a short-cut pathway of wastewater and clogging of the fixed bed can be prevented.

Figure 5A:
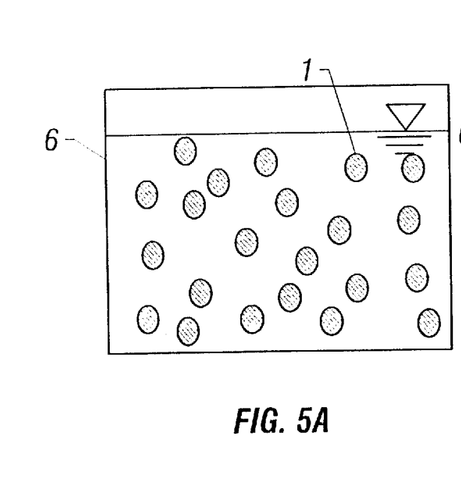
FIG. 5A to FIG. 5C are drawings illustrating the outline of a method of utilizing the microorganisms-immobilized magnetic carriers of the present invention as improving materials for wastewater treatment or as seeding materials.
Figure 5B:
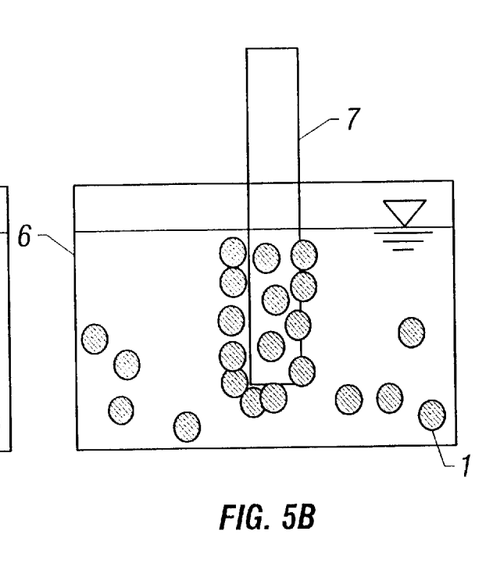
Figure 5C:
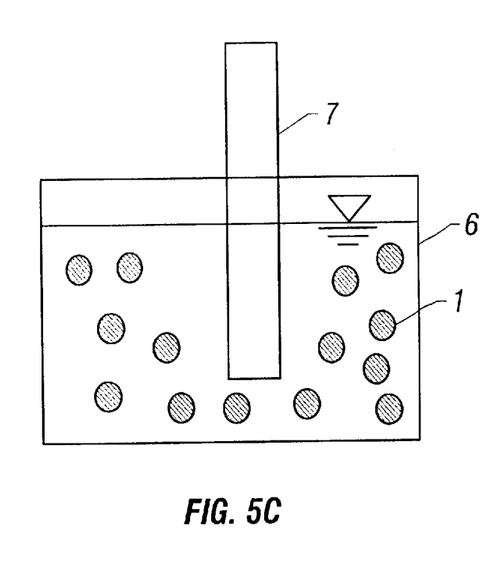

Example 7
Utilization of Microorganism-Immobilized Magnetic Carriers as Treatment-Improving Material or Seeding Material The porous microorganisms-immobilized magnetic carriers 1 obtained in Example 1 were introduced into culture chamber 6, and the microorganisms were cultured in the most suitable conditions for their growth. The magnetic carriers having a sufficient amount of the microorganisms immobilized thereon were stocked (FIG. 5A). Then, strong electromagnet 7 was introduced into the culture chamber 6 to recover the magnetic carriers 1 (FIG. 5B), and the recovered magnetic carries 1 were introduced to the treatment chamber 2 as treatment-improving material or seeding material (FIG. 5C).

Figure 6:
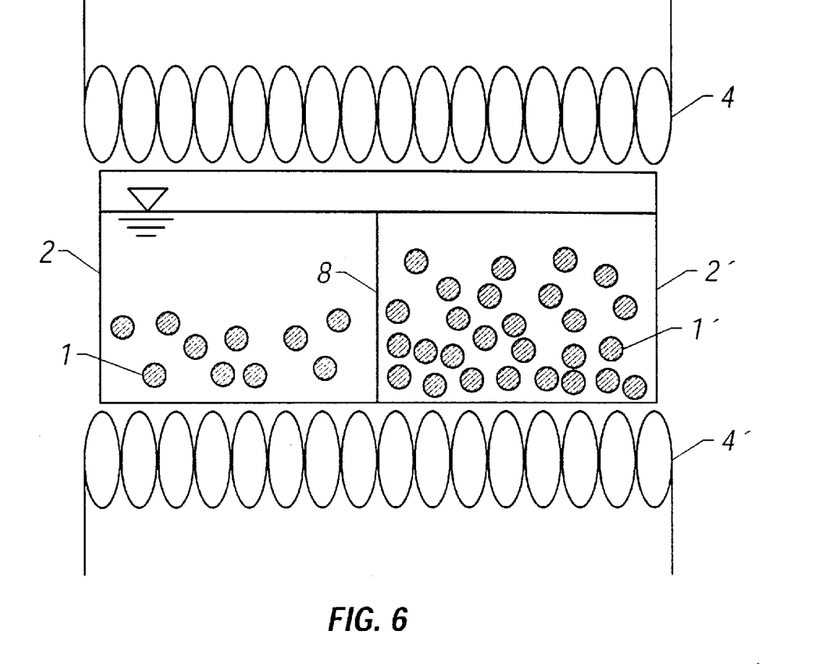
FIG. 6 is a drawing illustrating the outline of a method of utilizing the microorganisms-immobilized magnetic carriers of the present invention in a mixed culture system for treatment of wastewater.

Example 8
Utilization of Microorganism-Immobilized Magnetic Carriers in Mixed Culture Type Treatment Acid-producing bacterium-immobilized magnetic carriers 1 and methane-producing bacterium-immobilized carriers 1' stocked according to the method of Example 7 were retained and cultured in treatment chambers 2 and 2' respectively (FIG. 6). Because the growth rate of the methane-producing bacteria was considerably lower than that of the acid-producing bacteria, a larger amount of the methane-producing bacterium-immobilized carriers 1 was introduced to the treatment chamber 2'. An upward magnetic field was applied by sending electric current into the magnetic coil 4 over the treatment chambers 2 and 2'. Then, the electric current into the magnetic coil 4 was stopped, and a downward the direction magnetic field was applied by sending electric current into the magnetic coil 4'. By switching the direction of magnetic field at few-second intervals in this manner, a fluidized bed or fixed bed was formed in each chamber. The transfer of wastewater from treatment chamber 2 to treatment chamber 2' was conducted by quantitative overflow via a notch provided in the upper part of partition plate 8.

Figure 7:
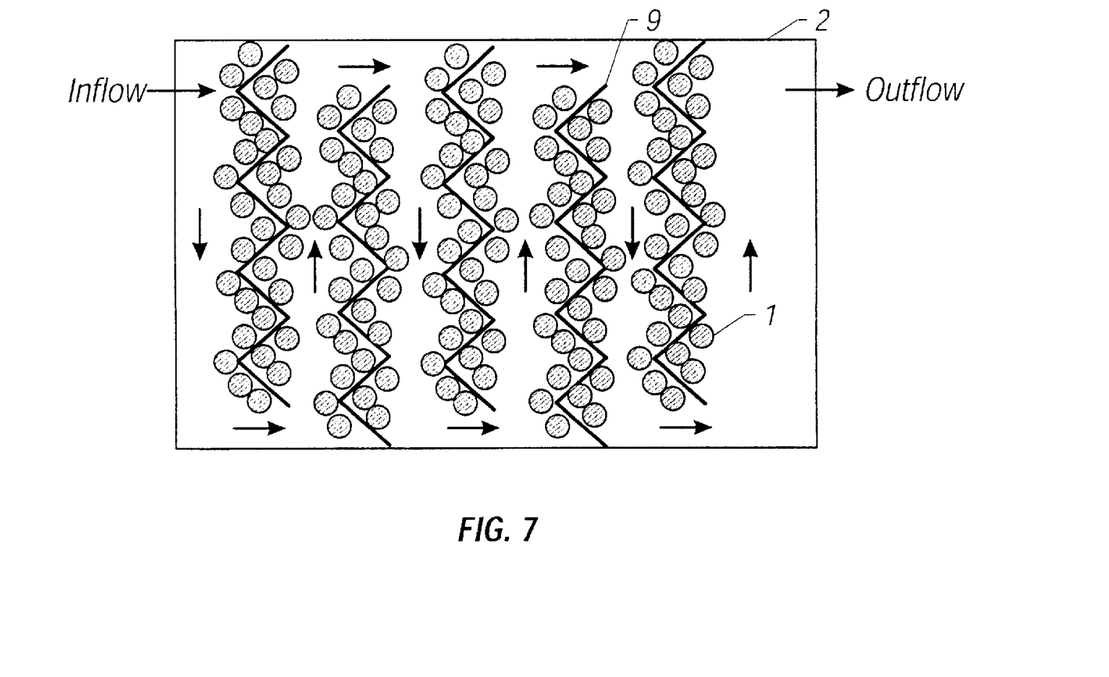
FIG. 7 is a drawing illustrating the outline of a method of utilizing the microorganisms-immobilized magnetic carriers of the present invention in wastewater treatment using an extrusion-type treatment chamber.

Example 9
Utilization of Magnetic Carriers in Extrusion-Type Treatment Chamber FIG. 7 is an upper sectional view of treatment chamber 2 provided with a plurality of permanent magnets 9. These magnets are corrugated to enlarge their surface area and also act as partition plates. By allowing a large amount of magnetic carriers 1 to adhere to the permanent magnets 9 with a broad surface area, and to be retained on them, the microorganisms can be kept at high concentration in the treatment chamber 2. Wastewater is passed by extrusion through the treatment chamber in the direction of the arrow, during which it is treated by the microorganisms immobilized on the magnetic carriers 1. Due to fixation by magnetic force, the magnetic carriers 1 are firmly retained, thus, even if wastewater is passed at considerably high speed, the carriers do not flow out.

Example 10
Removal of Nitrate Nitrogen by Batch Treatment Method Using Denitrificater-Immobilized Magnetic Carriers for Elimination of N in form of $NO_3^-$ (Nitrate Nitrogen)

Figure 8:
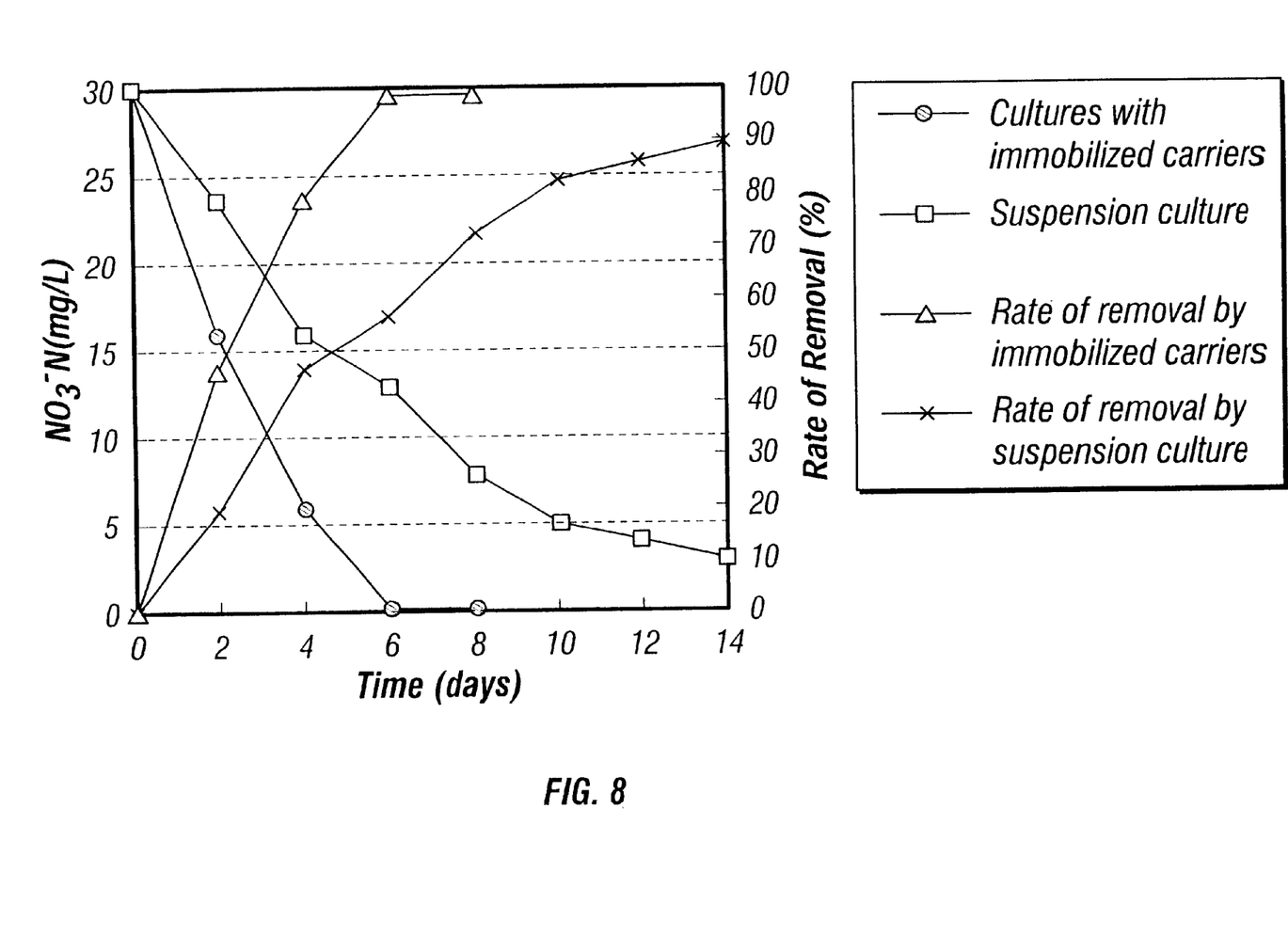
FIG. 8 is a graph showing a change with time in removal of nitrate nitrogen by porous denitrificater-immobilized magnetic carriers and non-immobilized denitrificater respectively.

Porous denitrificater-immobilized magnetic carriers were produced in the same manner as in Example 1. The porous denitrificater-immobilized magnetic carriers were used to treat wastewater containing N (in $NO_3^-$) at a concentration of 30 mg/L to examine a change with time in removal of nitrate nitrogen. As the comparative example, the denitrificater not immobilized on the carriers were used for treatment in the same manner to examine a change with time in removal of nitrate nitrogen. FIG. 8 shows the change with time in removal of nitrate nitrogen where the porous denitrificater-immobilized magnetic carriers and the non-immobilized denitrificater were used respectively. As can be seen in FIG. 8, the denitrificater-immobilized magnetic carriers of the present invention demonstrate about 4-times higher rate of removal of nitrate nitrogen than the non-immobilized denitrificater, indicating efficient treatment.

Example 11
Removal of Nitrate Nitrogen by Fixed-Bet Treatment Method Using Denitrificater-Immobilized Magnetic Carriers for Elimination of N in form of $NO_3^-$ (Nitrate Nitrogen)

Figure 9:
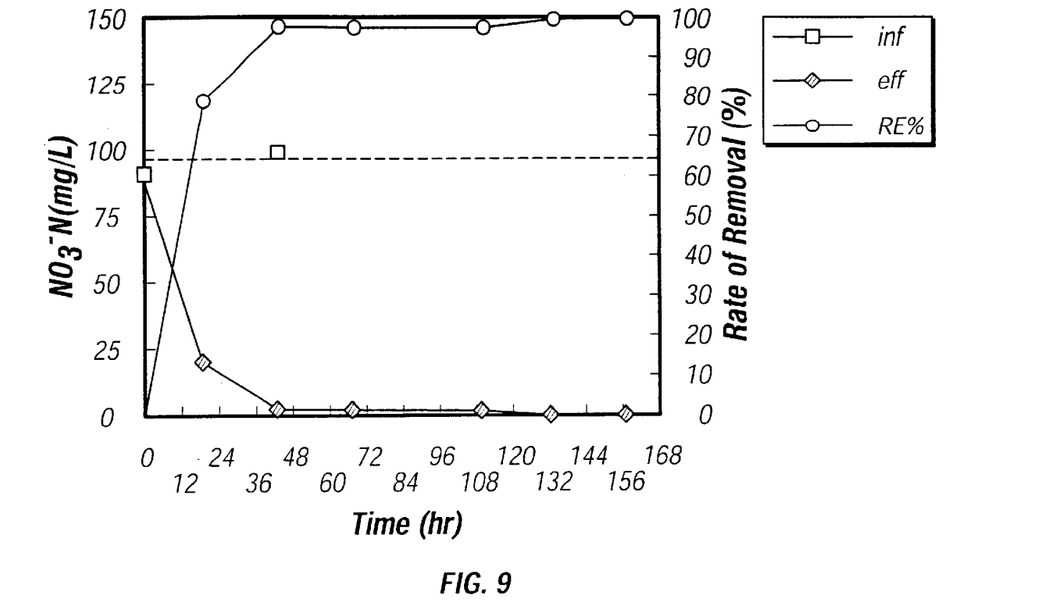
FIG. 9 is a graph showing a change with time in removal of nitrate nitrogen by porous denitrificater-immobilized magnetic carriers.

Porous denitrificater-immobilized magnetic carriers were produced in the same manner as in Example 1. The porous denitrificater-immobilized magnetic carriers were used to treat wastewater containing N (in $NO_3^-$) at a concentration of 90 mg/L by a continuous treatment method to examine a change with time in removal of nitrate nitrogen. FIG. 9 shows the change with time in removal of nitrate nitrogen by the porous denitrificater-immobilized magnetic carriers. As can be seen in FIG. 9, the magnetic carriers of the present invention demonstrate a high removal effect at about 40 hours after the operation was initiated. The hydraulic average retention time in this continuous treatment method was 24 to 30 hours.

Example 12
Removal of Nitrate Nitrogen by Batch Treatment Method Using Denitrificater-Immobilized PVA Magnetic Carriers for Elimination of N in form of $NO_3^-$ (Nitrate Nitrogen)

The porous denitrificater-immobilized PVA magnetic carriers obtained in Example 2 were used to treat wastewater containing N (in $NO_3^-$) at a concentration of about 85 mg/L to examine a change with time in removal of nitrate nitrogen. Said treatment was conducted by introducing 200 ml of said wastewater and 20 g of said porous denitrificater-immobilized PVA magnetic carriers into a 300-ml Erlenmeyer flask and stirring the mixture with a stirrer at 200 rpm.

Figure 10:
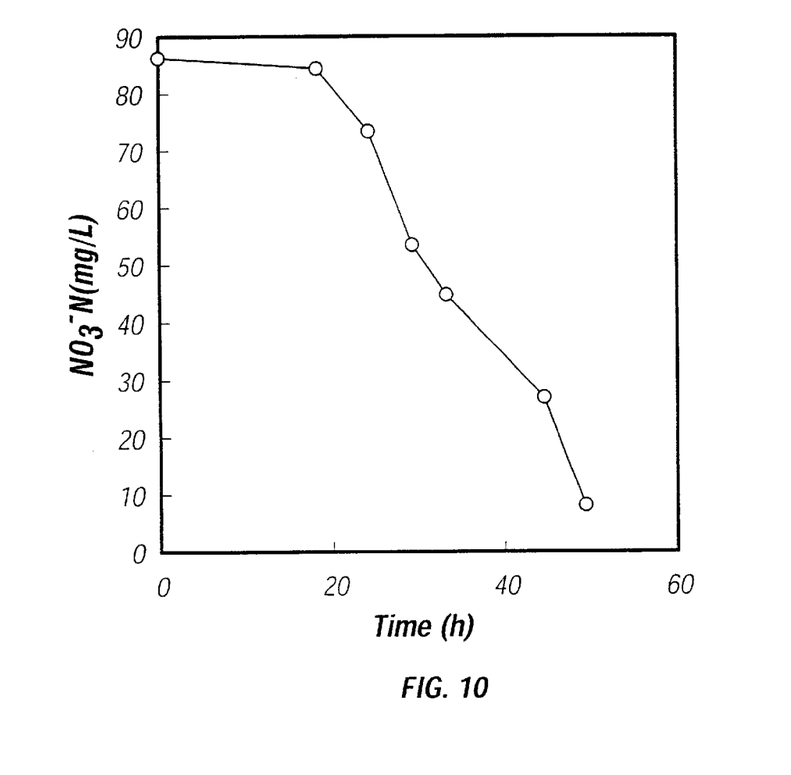
FIG. 10 is a graph showing a change with time in concentration of nitrate nitrogen by porous denitrificater-immobilized PVA magnetic carriers which contain 10 g/L (dry base) of denitrificater and 15 g/L of magnetite. The culture was degassed with the helium gas.

FIG. 10 shows the change with time in removal of nitrate nitrogen by the porous denitrificater-immobilized PVA magnetic carriers. As can be seen in FIG. 10, the porous denitrificater-immobilized PVA magnetic carriers demonstrate a high removal effect at about 40 to 50 hours after the operation was initiated.

What is claimed is:

1. A microorganism-immobilized magnetic carrier comprising an ultra-paramagnetic body and a microorganism entrapped in a polymer gel.

2. The microorganism-immobilized magnetic carrier of claim 1, wherein the polymer gel is a polyacrylamide.

3. The microorganism-immobilized magnetic carrier of claim 1, wherein the polymer gel is a polyvinylalcohol.

4. A method for treating wastewater comprising, introducing a microorganism-immobilized magnetic carrier into a treatment chamber containing a wastewater, wherein the microorganism-immobilized magnetic carrier comprises an ultra-paramagnetic body and a microorganism entrapped in a polymer gel, exposing the wastewater to the microorganism-immobilized magnetic carrier for sufficient time to treat the wastewater and then aggregating the microorganism-immobilized magnetic carrier.

5. The method of claim 4, wherein the magnetic carrier is aggregated by exposure to a magnetic field.

6. The method of claim 4, further comprising stirring the magnetic carrier by exposure to a magnetic field.

7. The method of claim 4, further comprising recovering the magnetic carrier.

* * * * *